United States Patent [19]

Fetto

[11] Patent Number: 5,259,249
[45] Date of Patent: Nov. 9, 1993

[54] HIP JOINT FEMORAL COMPONENT ENDOPROSTHESIS TEST DEVICE

[75] Inventor: Joseph F. Fetto, New York, N.Y.

[73] Assignee: New York University, New York, N.Y.

[21] Appl. No.: 950,546

[22] Filed: Sep. 25, 1992

Related U.S. Application Data

[63] Continuation-in-part of Ser. No. 688,408, Apr. 22, 1991, Pat. No. 5,211,666.

[51] Int. Cl.⁵ .............................................. G01N 3/00
[52] U.S. Cl. .......................................... 73/794; 73/849
[58] Field of Search ............................. 73/794, 818, 849

[56] References Cited

PUBLICATIONS

Smith, H. W. et al. An Osteoclast for Whole Bone Testing. 8th Annual Northeast Bioengineering Conference. Cambridge, MA, USA, (Mar. 27-28, 1980) pp. 1-4.

*Primary Examiner*—Jerry W. Myracle
*Attorney, Agent, or Firm*—Browdy and Neimark

[57] ABSTRACT

A femoral component of a hip endoprosthesis includes a lateral supporting wedge designed to be supported by the proximal lateral femur when in use. The wedge can be an integral part of the material of the femoral component or it can be placed on a standard component by cementing or preferably by a male/female socket fit. The lateral surface of the wedge forms an angle of about 10°-20° with the midline of the distal portion of the stem and has an anterior-posterior width of about 8.30 mm, preferably about 10-20 mm, and a medial-lateral extension of the lateral surface of the stem of at least 10 mm, preferably 10-30 mm. An apparatus for testing the endurance of femoral components includes a cable corresponding to the ilio-tibial band. Such an apparatus more accurately models hip biomechanics and thus permits a more accurate test of the stresses on femoral component designs.

1 Claim, 5 Drawing Sheets

HIP JOINT FEMORAL COMPONENT ENDOPROSTHESIS TEST DEVICE

CROSS-REFERENCE TO RELATED APPLICATIONS

The present application is a continuation-in-part of U.S. application Ser. No. 07/688,408, filed Apr. 22, 1991, now U.S. Pat. No. 5,211,666 the entire contents of which are hereby incorporated by reference.

FIELD OF THE INVENTION

The present invention relates generally to improvements in prosthetic devices, particularly hip prostheses. More specifically, the present invention relates to an improved prosthesis comprising the addition of a lateral load-transferring support surface designed to rest against the lateral femur when in use. The support surface can be an integral part of the material of the femoral component or it can be in the form of a wedge placed on a standard component by cementing or, preferably, by a male/female socket fit.

BACKGROUND OF THE INVENTION

Artificial or prosthetic devices for replacing defective joints in humans, particularly the hip joint, have been the subject of extensive research and development efforts for many years. In total hip arthroplasty, the most common adult reconstructive hip procedure currently performed in the U.S., a metallic femoral component is typically inserted into the natural medullary cavity of the femur. Simultaneously, an acetabular cup, usually of high-density polyethylene, is inserted into the acetabulum.

Figures 1, 8:
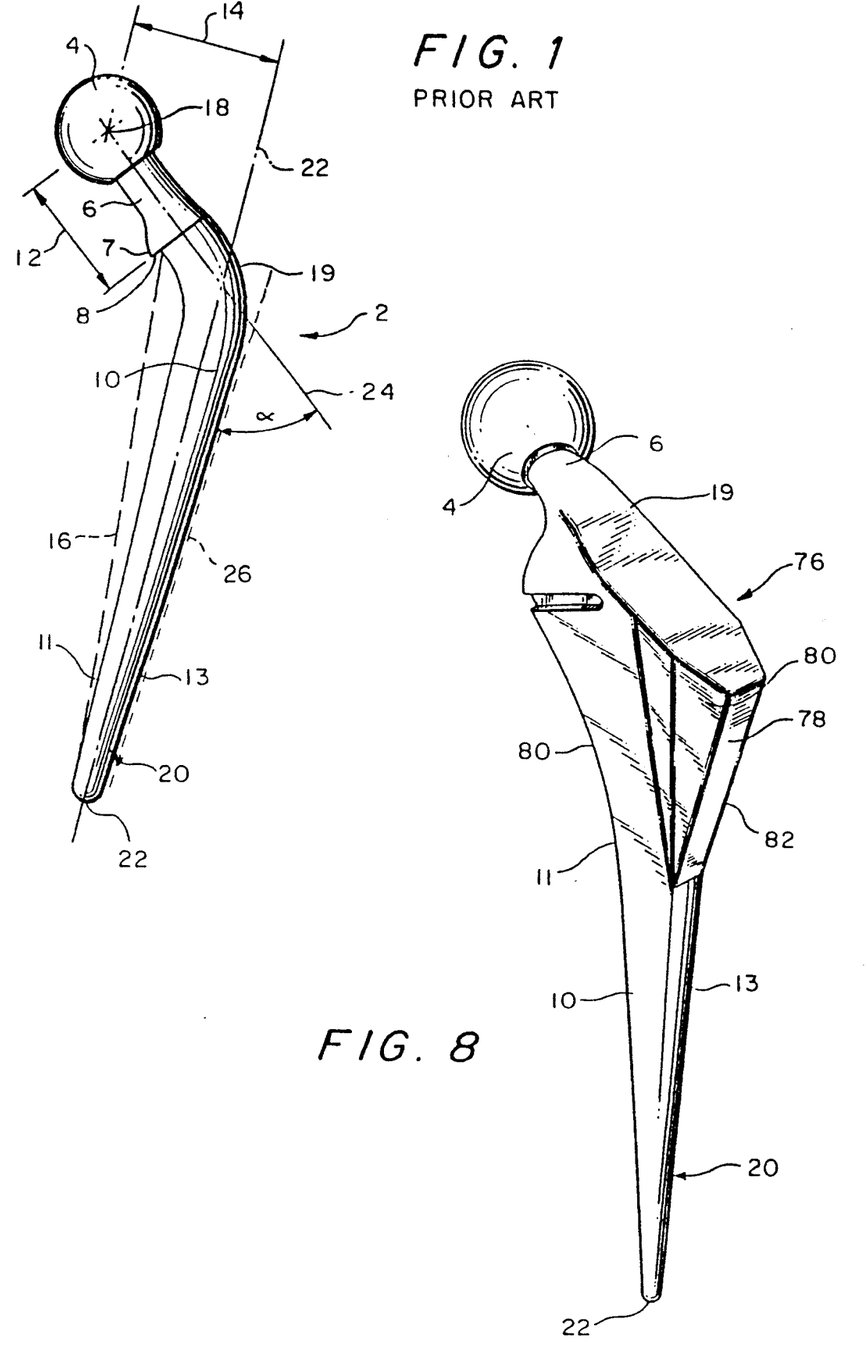
FIG. 1 is a side view of a conventional prior art femoral component.
FIG. 8 is a perspective view of one embodiment of a femoral component of the present invention.

A typical prior art femoral component 2 is shown in FIG. 1. The component 2 is an integral metallic component having a head 4, a neck 6 and a stem 10 having a medial side 11 and a lateral side 13. There is usually a collar 7 between the neck 6 and the stem 10. The medial extension of the collar 7 is the platform 8. The stem 10 has a proximal end 19 and a distal end 20 which ends at the tip 22. Various means of measuring such femoral components are used. The neck length 12 is measured from the center 18 of the head 4 to the base of the collar 7. The head-stem offset 14 is measured from the center 18 of the head 4 to the line 22 through the axis of the distal part 20 of the stem 10. The stem length 16 is measured from the medial base of the collar 7 to the tip 22 of the stem 10. The angle α of the neck 6 is measured by the angle at the intersection of the line 24 through the center 8 of the head 4 and the neck 6 with another line 26 along the lateral border of the distal half 20 of the stem 10.

The femoral component may be made of any strong inert material. Materials which have been used in the past on such components include stainless steel, chromium cobalt molybdenum alloy (Co-Cr-Mo), titanium, or a combination such as Co-Cr-Mo with a ceramic head or titanium with a cobalt-chromium or ceramic head. It may also be made of isoelastic polyacetate.

The head diameter is usually either 22, 26, 28, 32, or 38 mm with a neck length of 30-42 mm. The cross-section of the neck may be round, oval, or trapezoidal. The collar itself may or may not be present. The surface of the stem may be polished, dull, pre-coated with cement, press-fit, or have a porous-metal coating. There may or may not be fenestrations in the stem. The proximal third of the stem may be curved or angulated. The stem may be sabre-shaped, tapered, have a straight lateral edge or an anterior bow or a wide proximal third. The head-stem offset is generally 38-45 mm and the length is generally 12-18 cm or longer. Sometimes the femoral component is made as a modular system with a tapered metal post on the stem to mate with a head component that makes for different neck lengths and diameter of heads made of cobalt-chrome or ceramic. Reference is made to Calandruccio, R. A., "Arthroplasty of Hip"in *Campbell's Operative Orthopaedics,* Vol. 2, St. Louis, C. B. Mosby, 1987, chapter 41, pages 1213-1501.

A major problem from which most prior art femoral components suffer is stability of the component in place. Lack of complete stability can cause pain, failure of the artificial hip, fracture of the femur, or various other problems. Many attempts have been made to avoid such problems and add stability. One such attempt is the use of grouting medium or bone cement to fix the femoral component to the bone. In this case, bone is cleared from the medullary cavity to produce a larger space than required for the stem. Grouting material is inserted to fill the gap between the bone and the stem, as a means for fixing the device and as a means for load transfer between the device and the remaining bone.

While such a method is advantageous in that accurate insertion into the bone is not required and immediate mechanical fixation can be achieved leading to early weight bearing and rehabilitation, many disadvantages result from the inherent weakness of the cement which is exacerbated by poor distribution and/or contamination by blood during surgery.

Efforts have been made to fix implants without the use of a grouting medium, in which case it is important that an accurate bone resection be performed. The femoral component must be selected to give the tightest fit possible to provide a mechanically stable support for physiological loading.

Sometimes the surface of the implant is treated to provide a porous or roughened structure which acts to promote bone tissue growth around the implant, further stabilizing the femoral component with respect to the bone.

A major advantage of the latter system is the absence of cement or grouting medium, thus eliminating the long term inherent weakness and the short term toxic effects of these materials. The disadvantages are numerous. First, these stems have the added requirement of a sufficiently tight fit to prevent motion between metal and bone. Accurate bone resection customized to each type of available implant is difficult to achieve and often results in some initial looseness or lack of support. The implant will subsequently migrate to a more stable position, which may not be the ideal orientation for proper function of the femoral component. The requirement for a tight fit increases the possibility of fracture of the femur during insertion. Additionally, the patient must avoid bearing full weight on the hip for approximately six weeks to allow for bone formation.

Treatment of the implant to form the porous or roughened surfaces may cause local stress sites in the implant which significantly increase the risk of fatigue fractures. Further, a considerable time is required for bone tissue ingrowth and stabilization of the implant to occur. This is a significant detriment to early patient rehabilitation. Additionally, surface treatment exposes a greater surface area of the implant, increasing diffusion of metal ions which are associated with an increased risk of toxic or pathological effects.

The implant's stem may weaken from improper stress loads or decreased fatigue strength due to surface treatment. If this happens, the stem may bend or fracture, requiring its removal, which is particularly difficult if significant bone growth has occurred.

Various efforts have been made to design a femoral component hip endoprosthesis that can be implanted in the medullary canal in such a way as to provide implant stability without resorting to surface treatment. Some such efforts are directed to creating an isoelastic femoral component which is adaptable to the shape of the cavity created for the prosthesis in the femur and thus transfers the load from the implant outward to the bone surrounding the femoral component in the medullary canal. See, for example, U.S. Pat. No. 4,743,263. Other implants use stepped projections U.S. Pat. No. 4,031,571). Or fixation wires (U.S. Pat. No. 4,530,114) to impose tensile forces on the lateral side of the femoral component in the medullary canal. This is reportedly done to anchor the femoral component while taking advantage of the natural conditions of the bone.

Other efforts to stabilize implants have been directed to adding pins or studs (U.S. Pat. No. 3,896,505), winglike extensions to prevent rotation of the shank (U.S. Pat. No. 4,664,668), plates to provide anti-rotation stability for the implants (U.S. Pat. No. 4,904,269) and anti-rotation fins (U.S. Pat. No. 4,936,863). All of these efforts are directed to preventing the femoral component from rotating inside the medullary canal after insertion as force is applied to the implant by the patient returning to his or her feet.

Most of these implants suffer the disadvantage of prosthesis dislocation and bone fracturing due to improper force distribution on the femur.

Prior to the present invention, all implants have been designed based on the conventional assumption that the lateral femur is under tensile stress when unilateral loading forces are applied to the femur head. This assumption is based on the standard model for describing the biomechanics of the human hip described in the classic work of Koch, published in 1917 (*Am. J. Anat.* 21:177, 1917). He determined that the medial aspects of the femur are under compressive load during unilateral load, such as during a stride, and most of the lateral cortex is under tensile loading. In Koch's model, most of the force generated within the hip is attributed to the load of the abductor muscles, anatomically defined as taking origin from the lateral aspect of the iliac crest of the hip bone and inserting on the greater trochanter of the femur. Thus, the superimposed body weight creates a lever across the head of the femur, which serves as a fulcrum, with the body weight force being balanced by the abductor muscle force. This model leads to the conventional wisdom that the lateral aspects of the upper femur are under tensile loading.

In the design of femur components, it is advisable to subject every stem of each new design to static and dynamic testing. Such testing is necessary to ensure that a particular design does not fail prematurely due to fatigue. Thus, a need exists within the medical equipment industry to assess the endurance properties of femoral components of hip replacements and to provide a standard against which they can be prepared. The standards which have been used to date, however, are all based on the Koch model.

Figure 15:
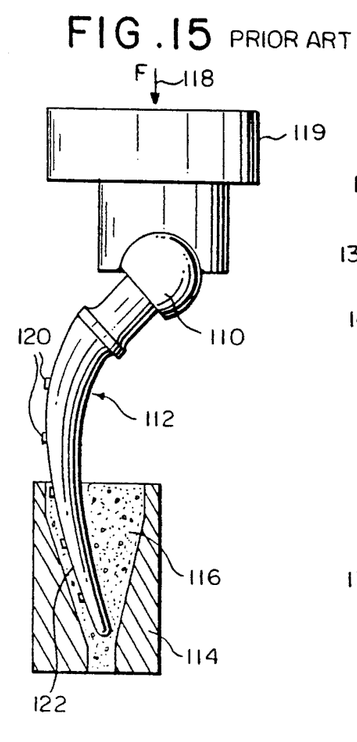
FIG. 15 is a front elevational view, partly in cross-section, of a conventional prior art stress measurement system.

The present standards and proposed standards are described in Humphreys, P. K. et al., "Testing of Total Hip Replacements: Endurance Tests and Stress Measurements Part I: Endurance Tests", *Proc. Instn. Mech. Engrs.*, 204:29-34 (1990) and Humphreys, P. K., et al., "Testing of Total Hip Replacements: Endurance Tests and Stress Measurements Part II: Stress Measurements, *Proc. Instn. Mich. Engrs.*, 204:35-41 (1990). Such measuring systems are also disclosed in Semlitsch, M. et al., "Ten Years of Experience With Test Criteria for Fracture-Proof Anchorage Stems of Artificial Hip Joints", *Engineering and Medicine*, 12:185-198 (1983). A diagram showing this conventional stress measurement system is shown in FIG. 15. In accordance with this testing procedure, the head 110 of the femoral component 112 to be tested is firmly clamped and inserted into a specimen holder 114 aligned in accordance with predetermined orientation angles. A fixing medium 116 is then poured into the holder 114 until it reaches a predetermined depth, usually about 50 mm below the collar of the stem. The specimen 112 is then left while the embedding medium 116 hardens. Epoxy resin is usually used as the embedding medium. The holder 114 with the fixed specimen 112 is then located in the testing machine and the entire stem may be immersed in a saline bath (not shown) in order to maintain physiological temperatures. The testing machine 119 then applies a load 118 vertically downward upon the head 110 of the femoral component of a predetermined amount and with a predetermined frequency. The vertical deflection is measured during the first minute of testing. A computer program controlling the load cycle is adjusted so that if the deflection exceeds 120% of the initial deflection, the testing machine will stop. Strain gauges 120 may be placed along the medial and lateral surfaces of the component stem 122 and the maximum bending stresses measured.

Dobbs, H. S. "A Model Femur for In Vitro Testing of Femoral Components", *J. Biomed. Eng.*, 3:225-34 (1981) discloses another model femur system for testing femoral components. This device uses a thin-walled tubular fixture of appropriate dimensions to simulate the femur. Strain gauges are placed on the stem as well as on the tubular structure. A three point bending test stand is disclosed in Reubin, J. D. et al., "Comparative Mechanical Properties of Forty-Five Total Hip Systems", *Clin. Orthop.*, 141:55-65 (1979).

Figure 16:
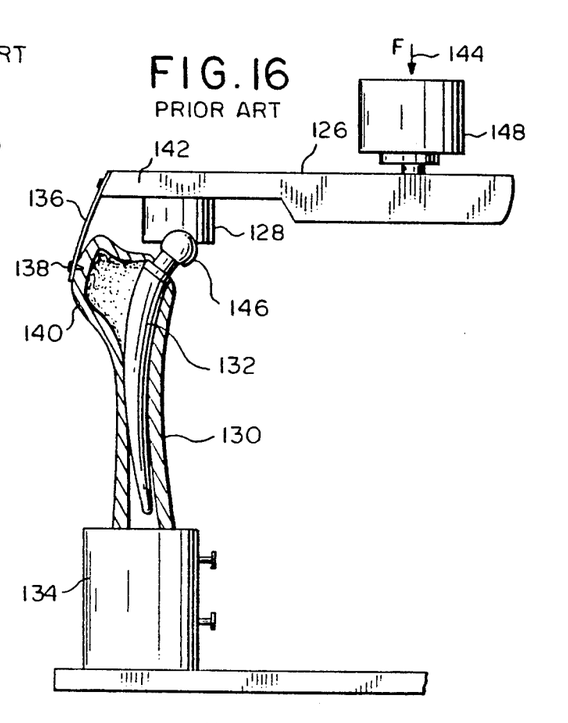
FIG. 16 is a front elevational view, partly in cross-section, of another prior art model femur system for testing femoral components.

In Tanner, K. E. et al., "A System for Modeling Forces on the Hip Joint in One-Legged Stance", *J. Biomed. Eng.*, 10:289-90 (1988), the authors recognize that the previous systems for testing of hips or hip prostheses using a single unidirectional load do not make allowances for the loads applied via the greater or lesser trochanters. Accordingly, Tanner proposed an experimental arrangement which more closely models the forces on the hip joint in one-legged stance, taking into account the abductor muscles between the iliac crest and the greater trochanter. This test system is shown in FIG. 16. This model uses a 200 mm U channel 126 to model the pelvis with a movable plastic "acetabulum" 128. A proximal section of a femur 130, suitably reamed, is implanted with an uncemented femoral component 132 and mounted vertically in a cylindrical holder 134, 150 mm from the line of action of the applied load. The abductors were modeled by a strip of stainless steel braid 136, screwed to the lateral aspect of the greater trochanter 140 using long cancellous bone screws 138. The braid 136 was then held at the end 142 of the U channel 126 at 20° to the vertical. Thus, when a load 144 was applied to the U channel 126 modeling the pelvis, the channel 126 remained approximately horizontal. The acetabular cup 128 was positioned to ensure that the femoral head 146 fitted into it with the "abductor tendon" 136 at the appropriate angle. Thus, when 83.5% of body weight was applied via the load cell 148 of a Schenk Trebel testing machine, the forces in the femur 130 and in the prosthesis 132 were supposed to be equivalent to those applied by standing on one leg so that the compressive force through the femoral head is reacted by a tensile force from the greater trochanter.

SUMMARY OF THE INVENTION

It is an object of the present invention to design a femoral component-hip endoprosthesis based on the more accurate model of hip biomechanics which establishes that the lateral aspects of the upper femur are under natural compression loading during the normal activities of standing and walking.

It is another object of the present invention to provide a femoral component having a lateral load-transferring surface which can transfer load to the internal lateral surface of the femur.

It is a further object of the present invention to provide such a femoral component in which said load-transferring surface is part of a lateral support wedge disposed at the upper lateral face of the femoral component stem.

It is yet another object the present invention to provide such a femoral component in which the lateral support wedge is integrally formed with the stem.

It is yet a further object of the present invention to provide such a femoral component in which the lateral support wedge is formed independently from the stem and then attached thereto, preferably with a male/female joint.

It is still another object of the present invention to provide a method and apparatus for testing femoral component designs based on the more accurate model of hip biomechanics which establishes that the lateral aspects of the upper femur are under natural compression loading during the normal activities of standing and walking.

These and other objects of the present invention have been attained due to the present inventor's discovery that the Koch standard model of hip biomechanics, upon which the design of all previous hip endoprostheses have relied, is incomplete and hence its conclusions regarding loading patterns are inaccurate. By using the more complete model of the biomechanics of the human hip developed by the present inventor, improvements in hip prostheses are accomplished which overcome the problems confronting the field.

The femoral component of the present invention is based on the discovery of the present inventor that the lateral aspects of the upper femur are under a compressive load, rather than a tensile stress as predicted by Koch. Thus, both the medial and lateral internal surfaces of the femur may be used as support surfaces for the femoral component. Accordingly, the femoral component of the present invention includes a lateral load-transferring support surface which is supported by the internal lateral surface of the upper femur when in use. The load transferring support surface is part of a wedge-shaped appendage on the lateral side of the proximal portion of the stem of the femoral component. This wedge-shaped appendage may be integral with the stem or may be formed separately and attached to a conventional femoral component by cement, screws, male/female socket fit or any other appropriate manner.

With knowledge that the lateral load-supporting surface will contact the internal lateral surface of the femur under compression at all times, the compressive load on the femoral component can be redistributed onto both sides of the femur to allow a safe and stable setting of the femoral component within the femur.

This knowledge of the more accurate biomechanical model of the femur allows a test device to be constructed which better fits this model, so as to more accurately test the stresses on femoral component designs.

BRIEF DESCRIPTION OF THE DRAWINGS

The accompanying drawings illustrate the invention. In such drawings.

DETAILED DESCRIPTION OF PREFERRED EMBODIMENTS

The embodiment of the present invention will now be described, by way of example, the scope of the invention being indicated in the claims.

As indicated above, previous models of the biomechanics of the hip ascribe most of the force generated within the hip to the load of the abductor muscles.

These models have substantially ignored the effect of the fascia lata/ilio-tibial band (ITB). This soft tissue connects the greater trochanter of the femur to the lateral portion of the proximal tibia and essentially functions as a guy wire. It reduces the tensile strains in the proximal femur by acting as a lateral tension band. The result is a compressive load throughout the femur.

Bone is not nature's optimal substance with which to resist tensile forces. Uncalcified collagen, i.e., tendon, has equal tensile strength to bone, with less weight. If the lateral aspect of the femur were under a purely tensile load, it would theoretically be composed of poorly calcified or uncalcified material, rather than relatively thick cortical bone. However, both radiological imaging and cadaveric dissections show relatively thick lateral cortical bone structure.

Figures 2, 3, 4, 5, 6:
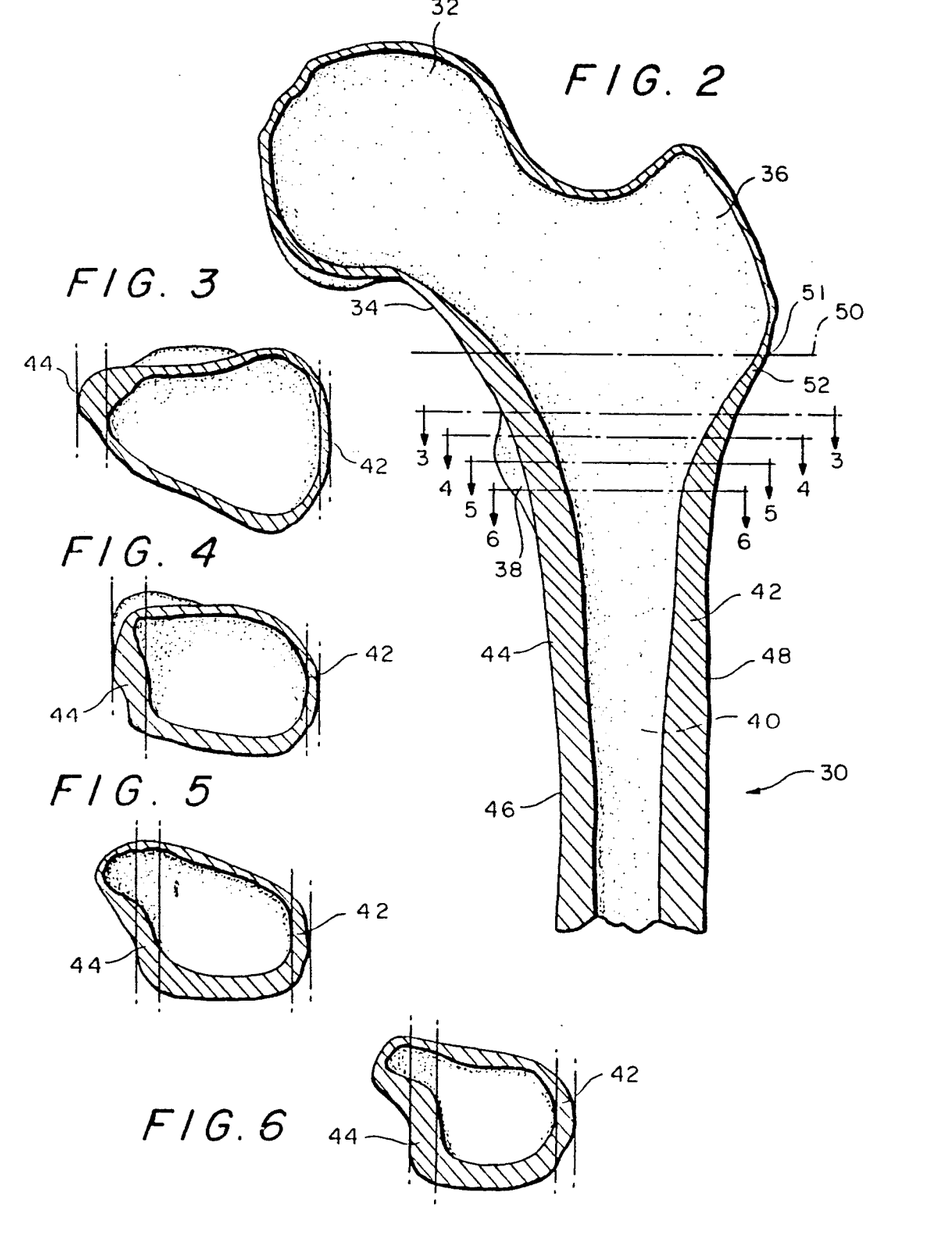
FIG. 2 is a longitudinal cross-sectional view of a femur.
FIG. 3 is a transverse cross-sectional view along lines 3—3 of FIG. 2.
FIG. 4 is a transverse cross-sectional view along lines 4—4 of FIG. 2.
FIG. 5 is a transverse cross-sectional view along lines 5—5 of FIG. 2.
FIG. 6 is a transverse cross-sectional view along lines 6—6 of FIG. 2.

The proximal half of a human femur 30 is shown in FIG. 2. The femur is comprised of the head 32, the neck 34, the greater trochanter 36, the lesser trochanter 38 and the medullary canal 40. The medial side 46 is the side of the femur 30 facing the midline of the body and the lateral side 48 is the side of the femur 30 toward the outside of the body. The cross-section of FIG. 3 is taken approximately 10 mm distal from the distal limit of the greater trochanter-forming wafer corresponding approximately to the level of the apophyseal scar 51, shown by line 50. The cross-sections of FIGS. 4, 5, and 6 are each approximately 5 mm distal to the previous cut.

Cadaveric transsections of five human femora were made at the levels of lines 3—3, 4—4, 5—5 and 6—6 and the width of the medial and lateral cortical bone present was measured. The measured widths of the medial 44 and lateral 42 cortical bone at the cross-sections of FIGS. 3-6 are shown in Table I.

TABLE I

|  | measured medial cortical bone (range) | measured medial cortical bone (mean) | measured lateral cortical bone (range) | measured lateral cortical bone (mean) |
| --- | --- | --- | --- | --- |
| FIG. 3 | 5.5–7.0 | 6.2 | 0.5–1.0 | 0.9 |
| FIG. 4 | 5.0–7.5 | 6.0 | 2.0–3.0 | 2.5 |
| FIG. 5 | 5.2–7.0 | 6.14 | 2.5–4.5 | 3.3 |
| FIG. 6 | 4.0–7.5 | 6.0 | 3.5–5.0 | 4.4 |

It can be seen that there is a significant amount of cortical bone mass in the lateral aspect 42 of the femur. This cortical bone mass begins with the inferior lateral aspect 52 of the greater trochanter 36 and coincides with the level of the apophyseal scar 51. The width of this cortical bone increases so that by 10 mm distal to the apophyseal scar, a point at approximately the level of the superior aspect of the lesser trochanter 38, it is more than 40% that of the medial cortex 44. With additional 5 mm increments, this lateral thickness increases to 50% and 73% of the medial cortical width, respectively. This ratio remains approximately constant with further distal sectioning of the femur, reducing only as one approaches the distal femur at the level of the lateral femoral epicondyle. These observations are consistent with the theory that the lateral aspect of the femur is under compressive load rather than tensile stress.

Thus, a model of the hip which includes the tension band effect of the ITB is consistent with femur bone morphology.

Figure 7:
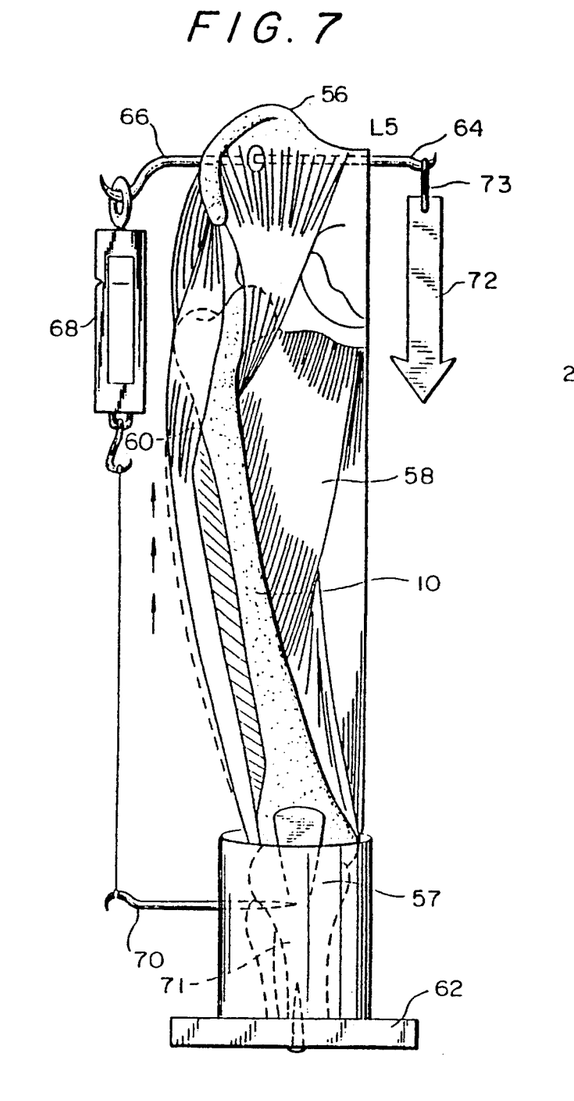
FIG. 7 is a front elevational view of a cadaveric dissection mounted on a test stand for performing a static test of the lateral fascial band.

In order to further demonstrate the effect of the ITB, a test was conducted of the static cadaveric loading of the human hemipelvis. The set-up for this test is shown in FIG. 7. A male cadaver was hemisected at L4 then sagittally sectioned through the pelvis 56. The leg was transected approximately 8 cm distal to the knee joint 57. The quadriceps femoris, including rectus femoris and sartorius muscles, were removed. The abductor muscles 58, hamstrings, iliopsoas, *tensor fascia lata* 60, *gluteus maximus* and *gluteus minimus* were left intact as were the smaller rotators of the hip joint. The gluteus medius was transected at its insertion on the greater trochanter and femur.

The specimen was mounted vertically on static test stand 62, approximately at the anatomic position of the leg in its normal seven degrees of knee valgus standing position, as shown in FIG. 7. A steel hook 64 was affixed at L5, and another hook 66 was placed through the ileum, projecting laterally.

A spring scale 68 was attached from the lateral pelvic hook 66 and anchored to another hook 70 which was secured to the tibia 71 approximately 4 cm below the knee joint 57, so as to parallel the lateral fascial band of the thigh (ITB). Serial weights 72 were attached by chain 73 to the pelvic hook 64 and the load registered on the lateral spring scale 68 was recorded. When the cadaveric specimen was serially loaded with weights of 2.2, 4.5 and 6.8 kg, a tensile force of 0.7, 1.5 and 2.3 kg was observed in the spring scale. This resistance was sufficient to prevent varus displacement and to maintain the equilibrium state during pelvic loading. Thus, when loading at the body's theoretical center of gravity, the ITB maintained a medial-lateral equilibrium state across the hip joint by exerting a tensile resistance. The efficiency of this resistance required the ITB to experience a ⅓ kg of tensile load for each kg of downward load applied to the pelvis. It was noted that the gluteus medius, having been sectioned, was not necessary for this equilibrium state to be maintained.

This model demonstrates, therefore, how lateral compressive loading does occur in the proximal femur and why there is such a significant amount of cortical bone mass in this region.

Mathematical analysis of the forces involved, when including the tension band effect of the ilio-tibial band, also confirms that the proximal-lateral aspect of the femur is under compressive load on unilateral stance rather than the previously expected tensile load.

Figure 17:
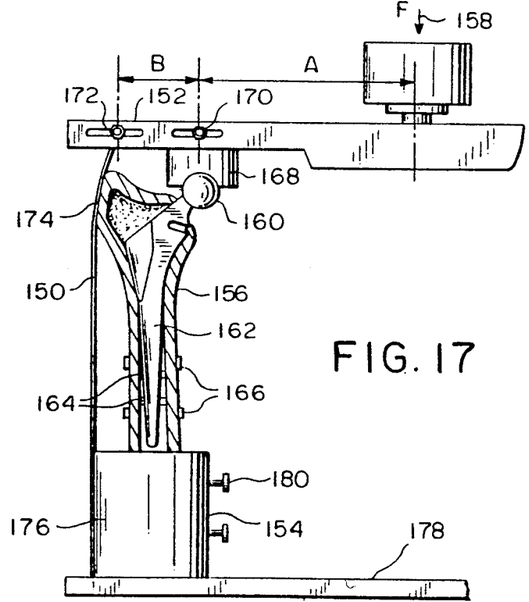
FIG. 17 is a front elevational view, partly in cross-section, of an apparatus for testing femoral component designs in accordance with the present invention.

The testing apparatus of the present invention takes into account the critical effects of the ITB. As shown in FIG. 17, the testing apparatus of the present invention is a substantial improvement over the model of Tanner et al. (FIG. 16), as it takes into account the ITB and the result is compression forces along the proximal lateral sides of the femur and the prosthesis. As seen in FIG. 17, a fixed cable 150 connects the load bar 152 with the fixed holder 154 at the distal end of the femur 156. The load 158 is applied to the bar 152 at a distance A from the center of the head 160 which is approximately twice the distance B from the center of the head to the point of attachment of the cable 150.

By including the cable 150, which approximates the function of the natural ITB, this testing device approximates stresses which will occur in the natural environment, which will be a much more accurate test of the device than the prior art systems discussed above. The femoral component 162 being tested may simply be inserted uncemented into the reamed femur 156 with strain gauges 164 being placed at preselected points on the femoral component in order to measure the stresses which occur upon application of the load. Strain gauges 166 may also be placed on the femur 156 itself, if desired. It is not necessary that an actual femur 156 be used in this test device. Other means to simulate the natural femur may be used, such as the tube of Dodds or the holder of Semlich and Humphreys. What is critical, however, is the presence of a cable 150 simulating the ITB and the offsetting of the load by an appropriate distance to simulate the forces on the hip joint in a one-legged stance which occur when taking into consideration the ITB.

While the ratio of about 2:1 of distance A to distance B remains substantially constant regardless of the size of the individual being simulated by the test stand, the actual distances used are selected so as to correspond as closely as possible to the actual physical distances in a person of a size for whom the femoral component is being developed. For example, distance A in a normal adult will usually be 110-120 mm. The acetabulum cup 168 is preferably made of plastic at its inner contact surface which has a concavity designed to match the curve of the femoral component head 160 with which it is to come into contact. The acetabulum cup 168 is adjustably mounted on the load bar 152 by means of slidable bracket 170. Similarly, the proximal end of cable 150 is adjustably mounted on the load bar 152 by means of a slidable bracket 172.

So that the forces will accurately simulate those to which the femoral component will be subjected when in use, the femur 156 in which it is implanted, or the synthetic equivalent thereof, has a trochanteric portion 174 with which the cable 150 comes into contact. The angle from the contact point with the trochanter 174 to the connecting point 172 with the load bar 152 will usually be about 20° from the vertical, the same as that for the abductor muscle discussed with respect to FIG. 16. The distal end 176 of the cable 150 is either connected to the holder 154 or the frame 178 to which the holder 154 is connected so as to simulate the joining of the ITB to the lateral portion of the proximal tibia. The holder 154 is designed to hold the femur 156 by means of clamps 180 or any other suitable means, such as cement, in a predetermined alignment, which alignment preferably substantially corresponds to that of the standing femur. The purpose of the test stand is to simulate the forces to which the femoral component will be subjected when in use when subjected to a one-legged stance such as occurs in the course of walking. Thus, with such a test stand, the femoral component being studied can be subjected to the conditions to which it will be subjected during use and the endurance properties of such a femoral component can be studied by means of the various strain gauges 164, 166.

Because the test stand of the present invention better simulates the actual forces to which the femur and the femoral component will be subjected when in use than any prior art test stand, it may be used to design and test all portions of the femoral component as well as various means of fixation of the femoral component to the femur.

Figure 9:
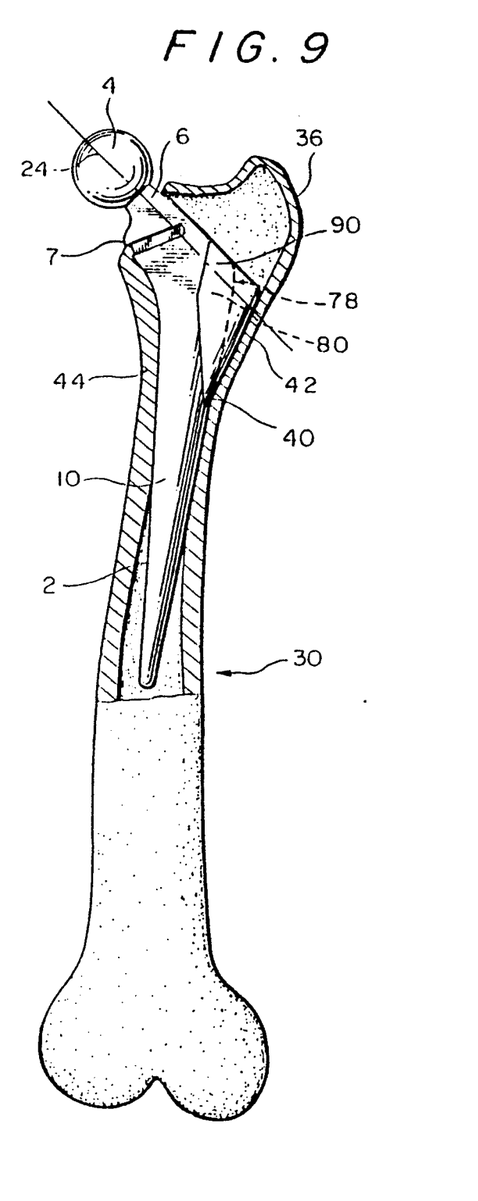
FIG. 9 is a side elevational view, partially broken away, of a femur with the femoral component of the present invention inserted in the medullary canal.

The hip endoprosthesis femoral component of the present invention was designed to take full advantage of the new knowledge that the proximal lateral cortex of the femur is under compressive load during unilateral stance. As seen in FIG. 8, the component 76 is designed with a lateral load transferring support surface 78 which contacts and rests on the lateral femur when in place (see FIG. 9), thus preventing subsidence and rotation after emplacement and distributing the loading forces more naturally along the femur.

By providing such improved stability and load distribution, there will be fewer prosthesis failures, less bone damage and subsequently fewer bone fractures.

In the embodiment of FIG. 8, the lateral support surface 78 is part of a wedge 80 fully integrated into the prosthesis 76. The femoral component 76 is otherwise conventionally comprised of a head 4, neck 6, and a stem 10 having a medial side 11, a lateral side 13, a proximal end 19, and a distal end 20. While no collar is present in the embodiment of FIG. 8, such may optionally be present.

The lateral support surface 78 should be large enough in conjunction with the stem 10, to transfer all lateral loading forces onto the upper third of the femur 30. The stem 10 and wedge 80 should form a tight proximal fit in the medullary canal 40 when downward force is applied. The downward force applied to the head 4 of the endoprosthesis will be transferred through the neck 6, stem 10 and lateral support wedge 80. The force will be subsequently distributed onto the medial cortex 44 and lateral cortex 42 of the femur 30. The force will be entirely compression force and not tensile or pulling force.

The lateral support surface 78 is not designed to penetrate or otherwise compromise the cancellous bone of the trochanter 36 either by a crushing or cutting action. Rather, the lateral support surface 78 is designed to rest against the lateral cortex 42 of the bone shaft. The lateral support wedge 80 is a fixed part of the endoprosthesis. It can be manufactured as one component, as in the embodiment of FIG. 8, or a retro-fit of a standard prosthesis as in the embodiments of FIGS. 10-14. The entire device 76 is inserted at one time.

As shown in FIGS. 10-13, the lateral support wedge 84 is manufactured as a separate entity which can be emplaced on a conventional femoral component 2 such as that shown in FIG. 1. In this embodiment, the support wedge 84 is maintained on the stem 10 by means of a male plug 86 disposed at the appropriate location on the proximal portion of the lateral stem 10 and a female socket 88 in the medial surface 87 of the wedge 84. This can be particularly seen in cross sectional view of FIG. 12. The wedge 84 preferably includes side wings 90 which extend beyond the lateral surface 87 and are shaped to correspond in shape to the corresponding surface of the stem 10. This provides additional contact surface between the wedge 84 and the stem 10. The placement of the wedge 84 on the surface .89 of the stem 10 can be further enhanced by means of an adhesive such as glue or cement.

Wedges 84 can be manufactured in various shapes and sizes so that the surgeon can select the appropriate combination of stem 10 and wedge 84 to make an appropriate prosthesis for the particular femur being fitted.

Figures 10, 11, 12, 13, 14:
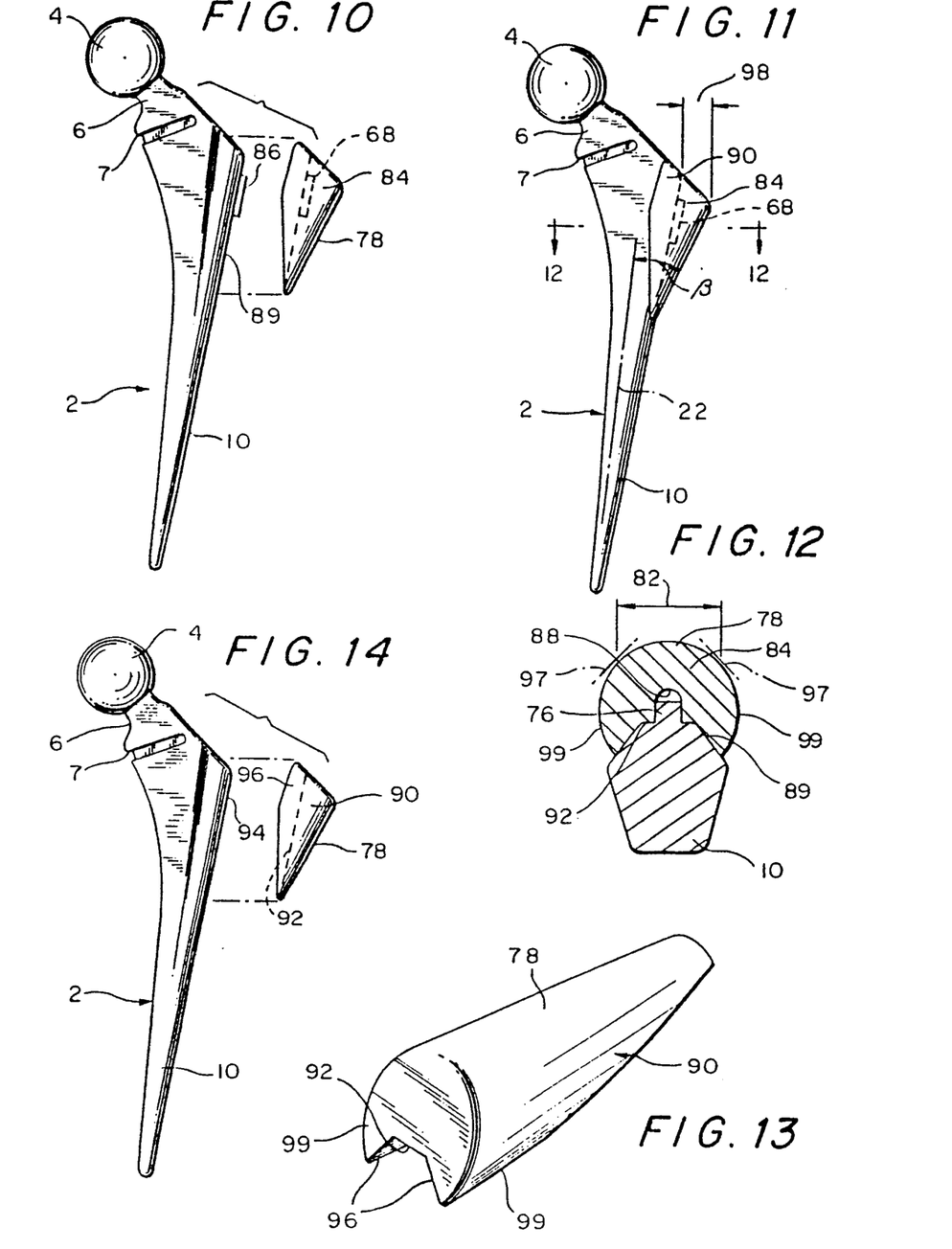
FIG. 10 is a side elevational view of a femoral component with a conventional stem and a supporting lateral wedge attachable by a male/female joint.
FIG. 11 is a side elevational view of the femoral component of FIG. 10 in assembled condition.
FIG. 12 is a transverse cross-section of the assembled femoral component of FIG. 12 along line 12—12.
FIG. 13 is a perspective view of a wedge usable in the embodiment of FIGS. 10 and 12.
FIG. 14 is a side elevational view of a femoral component with a conventional stem and a supporting lateral wedge attachable using glue or cement.

In FIG. 14, wedge 91 is also manufactured as a separate component but without the female socket 88 as is used on the wedge 84 of FIGS. 10-13. Similarly, no male plug 86 need be disposed on stem 10. In the embodiment of FIG. 14, the lateral support wedge 91 is affixed to the surface 94 of the stem 10 solely by means of an appropriate adhesive, such as glue or cement. The medial surface 92 and the internal surfaces of the wings 96 of the wedge 91 are designed to match and attach to the lateral surface 94 of the stem 10.

In all of the embodiments of the present invention, the lateral support surface 78 should have an anterior-posterior (A.P) width 82 which is large enough to provide sufficient support when contacting the internal surface of the lateral cortical bone, without acting as a stress riser which might violate or compromise the integrity of the bone. Preferably, the A.P width 82 of the support surface 78 should be at least 8 mm, preferably 10-20 mm, although it may be as wide as 30 mm. The use of the terms anterior, posterior, medial and lateral with respect to a femoral component throughout the present specification and claims refers to the respective directions when the component is in place in a human femur, as designed. If the A.P width of the support surface 78 is too narrow, such as the width of the rotation preventing fins in the prior art, then it will act as a knife and cut the bone rather than transfer the load forces. The width 82 may be substantially the same as the medial support surface of the stem 10 below the collar 7.

The support surface 78 of the wedge 80 is preferably slightly rounded so as to approximate the radius of curvature of the internal geometry of the lateral surface of the medullary canal from about the level of the lesser trochanter to about the level of the apophyseal scar, such as is shown in the embodiments of FIGS. 9-14. Such a curvilinear surface gives better surface contact, thus permitting superior load transmission. Furthermore, because of the anterior-posterior contact with the internal femoral cortex at the edges of the bulge 99 at the sides of the wedge 84, additional anti-rotational or torsional support is obtained. When the support surface 78 is rounded, the A-P width 82 is measured as a cross-section between the points 97 (see FIG. 12) on the surface of the wedge at which the tangent to the curve forms an angle of 45° with the horizontal.

The medial-lateral (M-L) breadth 98 of the wedge 84 from the surface 92 to the lateral surface 78 at its broadest point (see FIG. 11) should be at least 10 mm, preferably 10-30 mm, most preferably 15-20 mm. In the embodiment in which the wedge 80 is integral with the stem 10, the M.L breadth is measured in a corresponding manner, i.e., it extends what would otherwise have been the lateral surface of the stem by at least 10 mm. This breadth is optimal for the prevention of subsidence of the component when in use, over the course of time.

The angle $\beta$ between the support surface 28 and the midline 22 of the distal stem 20 is about 5°-20°, preferably about 10°-15°. Such an angle permits optimal transfer of the lateral loading forces onto the femur.

While some prior art prostheses have a lateral surface which is incidentally at an angle of about 5°-20° with the midline of the distal stem, this has always been for reasons other than serving as a lateral support surface, which is the purpose of the present invention. Such prior art prostheses have other elements which are critical to the disclosed purpose for the lateral surface angle in the prior art, usually to create some sort of load transfer to the anterior and posterior intertrochanteric region of the femur when in use, particularly at the medial and central portions of the A-P surfaces. For example, U.S. Pat. No. 4,840,633 to Kallabis et al discloses a femoral endoprosthesis which utilizes a screw spindle with a broad-flanged helical flank. The purpose of the flank is to project outwardly from both side faces of the stem and cut into the cortex of the anterior and posterior internal bone structure of the femur for improved proximal load transmission. To make room for the helical flank, the lateral surface of the proximal stem extends at an angle to the midline of the distal stem which may be within the range contemplated by the present invention. However, the present invention does not need a helical flank and such is to be expressly avoided in the present invention. Without such a helix, Kallabis et al would teach no reason to include a lateral surface with such an angle.

Similarly, the femoral endoprosthesis of U.S. Pat. No. 4,659,067 to Fournier, shows a lateral surface which appears to have an angle of about 10°. However, the lateral surface comes to a point and does not include a load-bearing surface. Thus, this device is similar to the devices with thin anti-rotational fins (such as U.S. Pat. No. 4,936,863). Furthermore, Fournier requires oblique load-transfering projections on the anterior and posterior faces which are not included in the present invention.

U.S. Pat. No. 4,778,475 to Ranawat et al discloses a femoral endoprosthesis with a wedge-shaped proximal portion in the intertrochanteric region which engages, for load transmission, the anterior and posterior endosteal surfaces of the femur, across the entire medial-lateral width thereof. Thus, the intention of Ranawat at is to transmit loads to the anterior and posterior femoral surfaces, which is contrary to the present invention which is designed to transmit loads to the medial and lateral femoral surfaces. The neck of Ranawat extends obliquely medially, anteriorly and superiorly from the proximal portion. This patent erroneously states that the bone is under tension at the proximal lateral aspect. Indeed, the design is intended to minimize load transfer apart from the lateral distal tip and the region generally corresponding to the porous-coated recess shown in FIG. 7 of Ranawat. Because of the unusual oblique angle of the neck to the stem it is difficult to measure the angle of the proximal lateral surface to the midline of the distal stem. However, the present invention expressly avoids the use of a wedge shape of the anterior and posterior faces of the proximal stem at the medial and central portions thereof as well as the oblique angularity of the plane of the neck with the plane of the stem. Without these unusual features of Ranawat et al, there would be no reason to utilize a lateral surface with an angle of about 5°-20° with the midline of the distal stem.

As opposed to these prior art prostheses, the femoral component of the present invention needs no structure specifically designed to transfer load to the anterior and posterior intertrochanteric region of the femur when in use. The bulge 99 of the wedge 84, shown particularly in FIGS. 12 and 13, may inherently cause some load transfer to the A.P surfaces of the femoral cortex and this is indeed advantageous as such contact prevents torsional forces. However, there is no such bulge or wedge on the A-P surfaces of the medial and central portions of the proximal stem. This feature clearly distinguishes the femoral component of the present invention from the components shown, for example, in the Kallabis and Ranawat patents.

While the design of the wedge 80 having the lateral support surface 78 when in place on the femoral component of the present invention has been discussed above with respect to particular angles and dimensions, those of ordinary skill in this art will understand that the specific angles and dimensions may vary depending on the size of the femur of the patient and other individual factors. However, the most important factor in the design with respect to the present invention is lateral supporting contact of the lateral support surface 78 of the wedge 80 on the internal surface of the lateral cortical bone from about the level of the lesser trochanter to about the level of the apophyseal scar. More particularly, such contact should occur at least at the point of intersection of the midline of the stem with the lateral surface of the medullary canal, which lateral surface will normally be approximately perpendicular to said midline at that point. If the support surface 78 of the wedge 80 is in contact with the lateral surface of the medullary canal at that point, then this will ensure proper force distribution when the effect of the ITB is taken into account. As indicated above, the greater the width of the surface contact, the better the load transmission. Thus, any femoral component which is not designed and dimensioned such as to contact the lateral portion of the medullary canal at the point of intersection of the medullary canal with the line representing the midline of the stem of the femoral component will not fall within the scope of the preferred embodiment of the present invention.

The femoral prosthesis of the present invention may optimally be designed intraoperatively in the manner described by Mulier, J. C. et al., *Clin. Orthop.*, 249:97–112 (1989). In such a method, a mold is made of the prepared femoral cavity which is accurately and thoroughly made using a laser. The femoral component is designed and manufactured while the operation is in progress using state-of-the-art computer and machining techniques. By such a method, the femoral component may be designed and manufactured such that the lateral support surface of the wedge exactly matches the surface of the medullary canal opposite the stem of the component so as to have optimum surface contact for compressive force distribution.

Furthermore, in view of the fact that it is now known that all portions of the femoral component are under compressive force, biocompatible materials other than metals may be used to make the femoral component, such as, for example, ultra-high molecular weight polyethylene, epoxy graphite, zirconia or alimunia ceramics, carbon fiber reinforced polyethylene-hydroxyapatite, etc. Some of these materials better lend themselves to the computer-aided manufacturing techniques of custom prostheses created intraoperatively as discussed above. All of these may readily be tested using the test stand of the present invention.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. Apparatus for testing endurance properties of the femoral component of a hip endoprosthesis, comprising:
   holder means for holding the femoral component to be tested in a predetermined alignment substantially corresponding to that of a standing femur;
   a substantially horizontal load bar having upper and lower surfaces;
   acetabulum means connected to the lower surface of said load bar for engaging the head of the femoral component to be tested;
   force means for applying downwardly directed force to a point on the upper surface of said load bar which is horizontally displaced from the location of said acetabulum means on said load bar; and
   a fixed cable connected at one end to said load bar at a position thereon which is horizontally displaced from the location of said acetabulum means on said load bar on the opposite side of said acetabulum means as the point of application of said force means, the other end of said fixed cable being connected to said holder means at a point corresponding to the distal end of the corresponding standing femur, wherein the point of application of said force means is approximately twice as far from said acetabulum means as is the distance from said acetabulum means to the point of connection of said cable to said load bar.

* * * * *